United States Patent
Matsumura et al.

(10) Patent No.: US 12,350,065 B2
(45) Date of Patent: Jul. 8, 2025

(54) ORAL FUNCTION VISUALIZATION SYSTEM, ORAL FUNCTION VISUALIZATION METHOD, AND RECORDING MEDIUM

(71) Applicant: Panasonic Intellectual Property Management Co., Ltd., Osaka (JP)

(72) Inventors: Yoshihiro Matsumura, Osaka (JP); Junko Nakajima, Osaka (JP); Masashi Ishimaru, Osaka (JP); Jakusei Kiyosaki, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 499 days.

(21) Appl. No.: 17/797,664

(22) PCT Filed: Feb. 5, 2021

(86) PCT No.: PCT/JP2021/004380
§ 371 (c)(1),
(2) Date: Aug. 4, 2022

(87) PCT Pub. No.: WO2021/166695
PCT Pub. Date: Aug. 26, 2021

(65) Prior Publication Data
US 2023/0000427 A1   Jan. 5, 2023

(30) Foreign Application Priority Data
Feb. 19, 2020   (JP) ................. 2020-026166

(51) Int. Cl.
*A61B 5/00*   (2006.01)
*A61B 1/24*   (2006.01)
*G10L 25/66*  (2013.01)

(52) U.S. Cl.
CPC .............. *A61B 5/4803* (2013.01); *A61B 1/24* (2013.01); *G10L 25/66* (2013.01)

(58) Field of Classification Search
CPC ......... A61B 5/4803; A61B 1/24; G10L 25/66; G10L 25/69; G10L 25/75; G10L 25/78; G10L 25/87; G10L 25/90; G10L 25/93
(Continued)

(56) References Cited

U.S. PATENT DOCUMENTS

| 2004/0109571 A1 | 6/2004 | Yoshimine |
| 2009/0305203 A1 | 12/2009 | Okumura et al. |

(Continued)

FOREIGN PATENT DOCUMENTS

| CN | 105261246 A | 1/2016 |
| JP | 06-348297 A | 12/1994 |

(Continued)

OTHER PUBLICATIONS

International Search Report issued in corresponding International Patent Application No. PCT/JP2021/004380, dated May 11, 2021, with English translation.

(Continued)

*Primary Examiner* — Aaron F Roane
(74) *Attorney, Agent, or Firm* — Rimon P.C.

(57) ABSTRACT

An oral function visualization system includes: an outputter that outputs information for prompting a user to utter a predetermined voice; an obtainer that obtains an uttered voice of the user uttered in accordance with the output; an analyzer that analyzes the uttered voice obtained by the obtainer; and an estimator that estimates a state of oral organs of the user from a result of analysis of the uttered voice by the analyzer. The outputter outputs, based on the state of the oral organs of the user estimated by the estimator, (Continued)

information for the user to achieve a state of the oral organs suitable for utterance of the predetermined voice.

10 Claims, 12 Drawing Sheets

(58) Field of Classification Search
USPC .......................................................... 600/301
See application file for complete search history.

(56) References Cited

U.S. PATENT DOCUMENTS

| | | |
|---|---|---|
| 2017/0206691 A1 | 7/2017 | Harrises et al. |
| 2019/0125243 A1 | 5/2019 | Oku et al. |

FOREIGN PATENT DOCUMENTS

| | | | | |
|---|---|---|---|---|
| JP | 2006-126498 A | 5/2006 | | |
| JP | 2007-122004 A | 5/2007 | | |
| JP | 2011-76044 A | 4/2011 | | |
| JP | 2015-145938 A | 8/2015 | | |
| JP | 2017-198922 A | 11/2017 | | |
| JP | 6491772 B | 3/2019 | | |
| JP | 2019-511067 A | 4/2019 | | |
| JP | 2019-165880 A | 10/2019 | | |
| KR | 20100107676 | * 10/2010 | ............ | G10L 21/10 |
| WO | 03/068062 A1 | 8/2003 | | |
| WO | 2013/031677 A1 | 3/2013 | | |
| WO | 2017/127571 A1 | 7/2017 | | |
| WO | 2018/003127 A1 | 1/2018 | | |
| WO | 2019/225241 A1 | 11/2019 | | |
| WO | 2019/225242 A1 | 11/2019 | | |

OTHER PUBLICATIONS

Takashi Nakaya, et al., "Swallow Exercise Support System with Kinect Sensor," IPSJ SIG Technical Report, vol. 2015-HCI-162, No. 12, Mar. 2015, 34 pages, with English translation.

Chinese Office Action dated Nov. 30, 2023 issued in the corresponding Chinese Patent Application No. 202180013561.3, with English translation of the Search Report.

* cited by examiner

FIG. 11

| Formant frequency / Sound | First formant frequency | Second formant frequency | Third formant frequency |
|---|---|---|---|
| a | 768 | 1306 | 2552 |
| i | 310 | 2146 | 2920 |
| u | 370 | 1230 | 2232 |
| e | 536 | 1824 | 2510 |
| o | 522 | 926 | 2565 |

- Image A
- Image B
- Image C
- Image D
- Image E

FIG. 12

| Process of eating and swallowing | | Sound(s) to be focused | Image display |
|---|---|---|---|
| Mastication phase | Opening and closing of mouth | "i", "e", and "a" | Present movement of pronunciation containing "i", "e", "a" |
| | Mastication | "ka la" | Present movement of pronunciation of "ka la" |
| | Lip closure | "p" | Present movement of pronunciation of "Pa Pi Pu Pe Po" |
| Oral transit phase | Forward tongue movement | "t" "e" | Present movement of pronunciation containing "t", "e" |
| | Back tongue movement | "k" "o" | Present movement of pronunciation containing "k", "o" |
| Pharyngeal phase | Tongue palate closure | "ko" | Present movement of pronunciation of "ko" |

1000

ORAL FUNCTION VISUALIZATION SYSTEM, ORAL FUNCTION VISUALIZATION METHOD, AND RECORDING MEDIUM

CROSS-REFERENCE OF RELATED APPLICATIONS

This application is the U.S. National Phase under 35 U.S.C. § 371 of International Patent Application No. PCT/JP2021/004380, filed on Feb. 5, 2021, which in turn claims the benefit of Japanese Application No. 2020-026166, filed on Feb. 19, 2020, the entire disclosures of which Applications are incorporated by reference herein.

TECHNICAL FIELD

The present disclosure relates to an oral function visualization system and an oral function visualization method.

BACKGROUND ART

Patakala exercises etc. have been used for the elderly and others having declining oral functions to train them to open and close their mouth or to practice pronunciation that strengthens their swallowing function. Patent Literature (PTL) 1 discloses an augmented reality system etc. that utilize reflections, which displays a view of a user's face and the like on a display.

CITATION LIST

Patent Literature

[PTL 1] Japanese Unexamined Patent Application Publication (Translation of PCT Application) No. 2019-511067

SUMMARY OF INVENTION

Solution to Problem

An oral function visualization system according to an aspect of the present disclosure is an oral function visualization system including: an outputter that outputs information for prompting a user to utter a predetermined voice; an obtainer that obtains an uttered voice of the user uttered in accordance with the output; an analyzer that analyzes the uttered voice obtained by the obtainer; and an estimator that estimates a state of oral organs of the user from a result of analysis of the uttered voice by the analyzer, wherein the outputter further outputs, based on the state of the oral organs of the user estimated by the estimator, information for the user to achieve a state of the oral organs suitable for utterance of the predetermined voice.

An oral function visualization method according to an aspect of the present disclosure is an oral function visualization method including: outputting information for prompting a user to utter a predetermined voice; obtaining an uttered voice of the user uttered in accordance with the outputting; analyzing the uttered voice obtained in the obtaining; estimating a state of oral organs of the user from a result of analysis of the uttered voice in the analyzing; and outputting, based on the state of the oral organs of the user estimated in the estimating, information for the user to achieve a state of the oral organs suitable for utterance of the predetermined voice.

A recording medium according to an aspect of the present disclosure is a non-transitory computer-readable recording medium having recorded thereon a program for causing a computer to execute an oral function visualization method including: outputting information for prompting a user to utter a predetermined voice; obtaining an uttered voice of the user uttered in accordance with the outputting; analyzing the uttered voice obtained in the obtaining; estimating a state of oral organs of the user from a result of analysis of the uttered voice in the analyzing; and outputting, based on the state of the oral organs of the user estimated in the estimating, information for the user to achieve a state of the oral organs suitable for utterance of the predetermined voice.

BRIEF DESCRIPTION OF DRAWINGS

FIG. 11 is a diagram illustrating an example of data that associates voice feature amounts and image data items used by the oral function visualization system according to the embodiment of the present disclosure.

FIG. 12 is a table showing the contents of video display corresponding to the eating and swallowing process according to the embodiment of the present disclosure.

DESCRIPTION OF EMBODIMENT

Hereinafter, an embodiment is described with reference to the drawings. Note that the following embodiment describes a general or specific example. The numerical values, shapes, materials, constituent elements, the arrangement and connection of the constituent elements, etc., illustrated in the following embodiment are mere examples, and are therefore not intended to limit the present disclosure. Also, among the constituent elements in the following embodiment, constituent elements not recited in any one of the independent claims will be described as optional constituent elements.

Note that the drawings are represented schematically and are not necessarily precise illustrations. Furthermore, in the Embodiment 1

[Voice Feature Amounts and Configuration of Inside of Oral Cavity]

Figure 1:
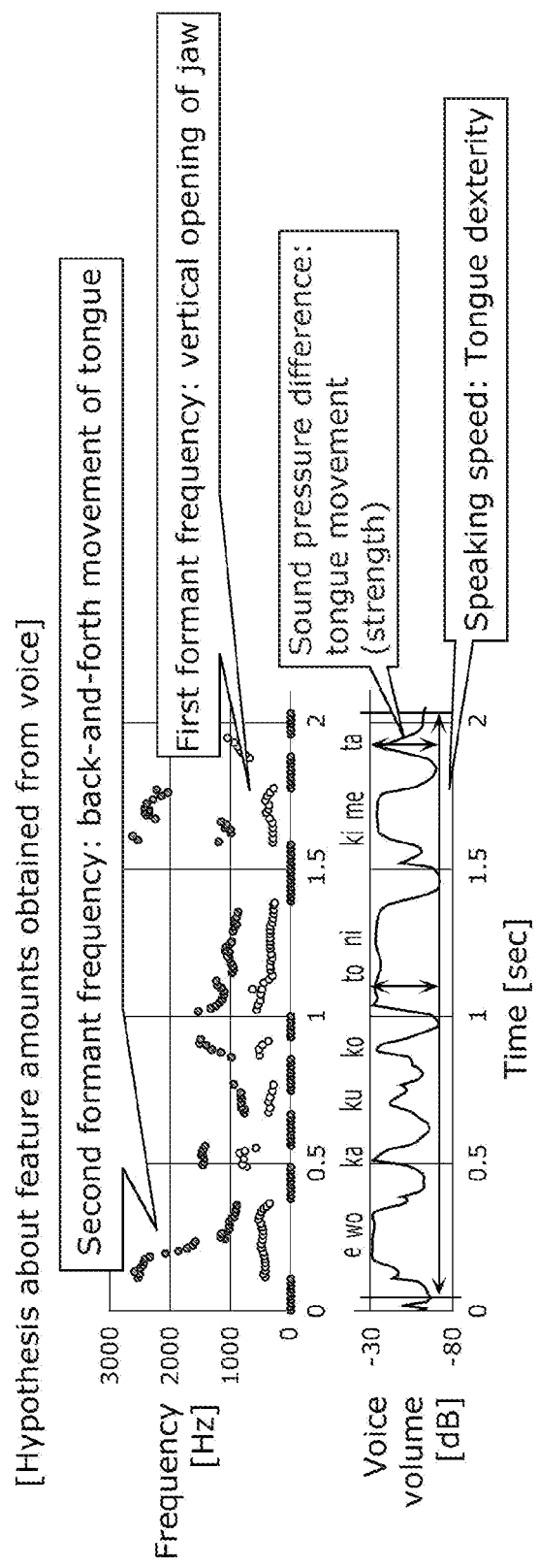
FIG. 1 is a diagram illustrating feature amounts obtained from a voice uttered by a human.

FIG. 1 is a diagram illustrating feature amounts obtained from a voice. Feature amounts obtained from the voice are a first formant frequency, a second formant frequency, a sound pressure difference, and a speaking speed. Plural peaks are identified in data that is obtained by converting voice data into frequency. The frequency of the peak having the lowest frequency among the plural peaks is first formant frequency F1. The frequency of the peak having the next lowest frequency after first formant frequency F1 is second formant frequency F2. The frequency of the peak having the next lowest frequency after second formant frequency F2 is third formant frequency F3. Each frequency is obtained by extracting a vowel part of an uttered voice by a known method and calculating the spectrum of the vowel part through data conversion of voice data of the extracted vowel part into the amplitude with respect to the frequency.

FIG. 1 illustrates an example of the first formant frequency and the second formant frequency. FIG. 1 illustrates an example of the case where a phrase "e wo ka ku ko to ni ki me ta" (I decided to draw a picture) is pronounced.

The first formant frequency is the peak frequency having the smallest amplitude counted from the low-frequency side of human voice, and is known to easily reflect voice features influenced by tongue movement (especially up-and-down movement). In addition, the first formant frequency is also known to easily reflect voice features influenced by the opening of the jaw.

The second formant frequency is the peak frequency having the second amplitude counted from the low-frequency side of human voice, and is known to easily reflect the influence of the position of the tongue (especially the front-back position) among the resonances produced by the vocal cord sound source in the vocal tract, the oral cavity such as lips and tongue, and nasal cavity, etc. In addition, for example, since it is not possible to speak correctly without teeth, the occlusal state of the teeth (a total number of teeth) in the oral preparatory phase is considered to influence the second formant frequency. Also, for example, since it is not possible to speak correctly with low saliva, the saliva secretion function in the oral preparatory phase is considered to influence the second formant frequency. The motor function of the tongue, the saliva secretion function, or the occlusal state of the teeth (a total number of teeth) may be calculated from either a feature amount obtained from the first formant frequency or a feature amount obtained from the second formant frequency.

The second formant frequency mainly represents back-and-forth movement of the tongue during pronunciation. FIG. 1 also illustrates an example of a sound pressure difference and a speaking speed. In pronunciation, the sound pressure difference mainly represents the strength of tongue movement. The speaking speed represents tongue dexterity.

In the graph illustrated in FIG. 1, changes in sound pressure corresponding to "e", "wo", "ka", "ku", "ko", "to", "ni", "ki", "me", and "ta" are identified. The oral function visualization system described below obtains the data illustrated in FIG. 1 as voice data representing the user's pronunciation. Using a known method, for example, the oral function visualization system calculates the sound pressures of "t" and "o" in "to" and the sound pressures of "t" and "a" in "ta" included in the voice data illustrated in FIG. 1. Oral function visualization system 10 also calculates the sound pressures of "t" and "o" in "to" as feature amounts.

In this way, the oral function visualization system extracts various feature amounts from the voice pronounced by the user.

Figure 2:
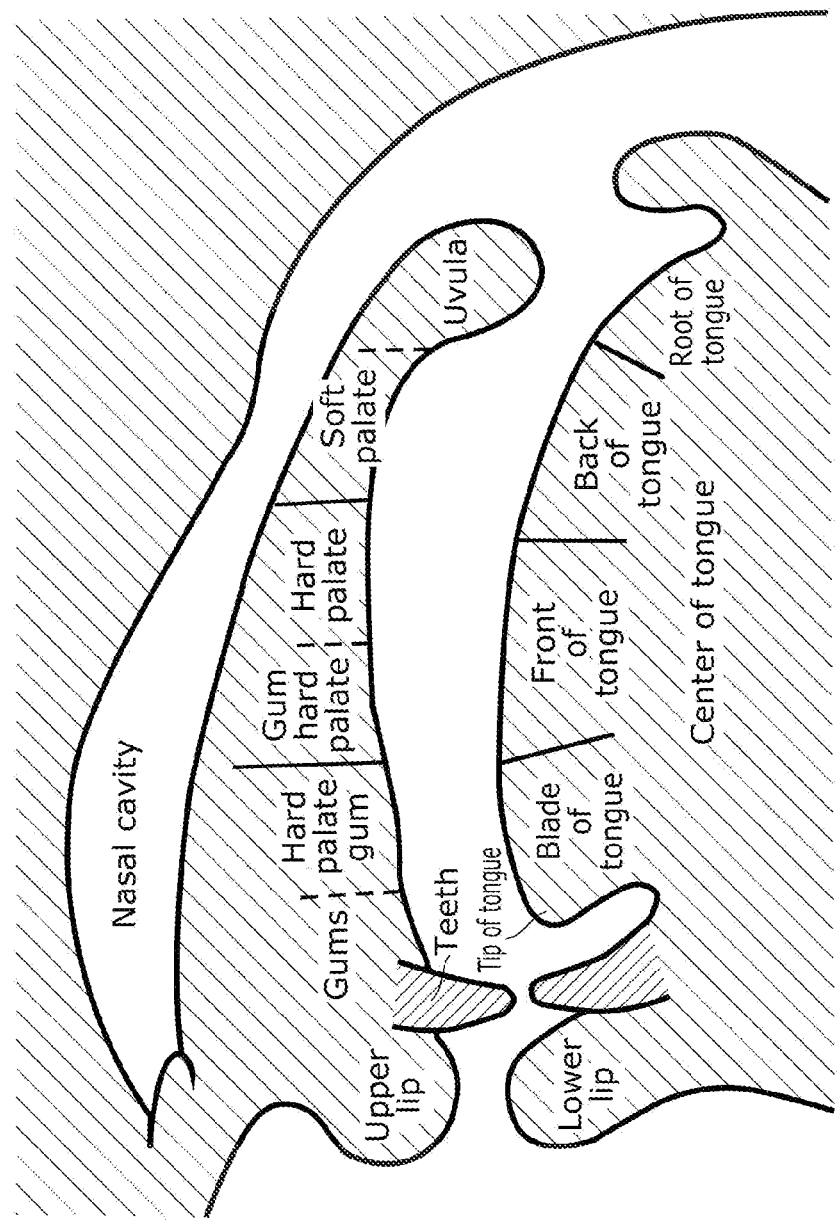
FIG. 2 is a diagram illustrating a configuration of the inside of the oral cavity of a human.

Next, the following describes a configuration of the inside of the oral cavity used when oral function visualization system 10 reproduces the inside of the oral cavity of user 2. FIG. 2 is a diagram illustrating a configuration of the inside of the oral cavity of a human. As illustrated in FIG. 2, the oral cavity includes, in order of proximity to the outside, the upper lip, lower lip, teeth, gums, and tip of the tongue. The tip of the tongue is followed by the blade of the tongue, front of the tongue, back of the tongue, and root of the tongue toward the back of the oral cavity. Also, the gums are followed by the hard palate gum, gum hard palate, hard palate, soft palate, and uvula. Oral function visualization system 10 models each of the parts enumerated here, analyzes user 2's pronunciation, and reproduces the position of each part. The reproduction need not be performed for all the parts inside the oral cavity, and may be performed for some of the parts inside the oral cavity.

[Configuration of Oral Function Visualization System]

Figure 3:
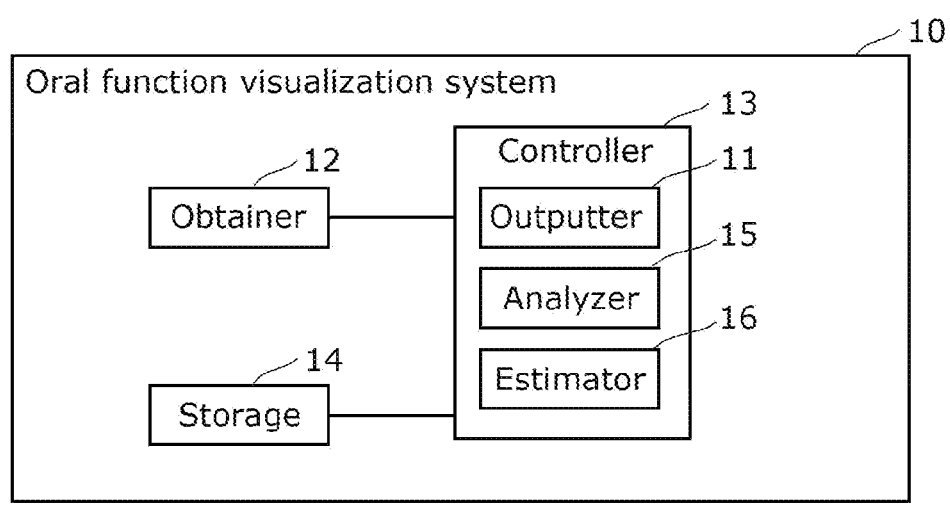
FIG. 3 is a block diagram illustrating a configuration of an oral function visualization system according to an embodiment of the present disclosure.

FIG. 3 is a block diagram illustrating a configuration of oral function visualization system 10 according to the embodiment of the present disclosure. Oral function visualization system 10 includes outputter 11, obtainer 12, controller 13, storage 14, analyzer 15, and estimator 16.

Outputter 11 outputs, to a screen, data such as the voice feature amounts of user 2's pronunciation analyzed by analyzer 15 or a reproduction image etc. of the inside of the oral cavity of user 2 estimated by estimator 16. Outputter 11 is implemented by a terminal, such as a display, capable of displaying an image on a screen, and a processor, microcomputer, or a dedicated circuit. The terminal may be a tablet terminal or a smartphone. The terminal may be a printer or the like in the case where oral function visualization system 10 outputs, for example, a state of the oral cavity of the user on paper. In addition to the image display function, outputter 11 may also have a function to output a voice realized by a loudspeaker or the like. Further, outputter 11 generates an image showing a state of the oral cavity of user 2 estimated by estimator 16. Outputter 11 outputs information for user 2 to achieve a state of the oral organs suitable for utterance of a predetermined voice. The information may be, for example, words or the like that instruct how to move the tongue or lips, etc. Alternatively, outputter 11 may generate information that prompts the user to do training to achieve a state of the oral organs suitable for utterance of a predetermined voice.

Obtainer 12 obtains voice data that is obtained by a microphone or the like collecting, in a non-contact manner, a voice uttered by user 2. The voice is a voice of user 2 who has uttered a predetermined syllable or a predetermined sentence or word. Obtainer 12 may further obtain personal information about user 2. For example, the personal information is information entered into a mobile terminal or the like, and is, for example, age, weight, height, gender, body mass index (BMI), dental information (e.g., a total number of teeth, whether or not a denture is used, the position of occlusal support, etc.), serum albumin level, or food intake rate. Obtainer 12 transmits the obtained data such as the voice to analyzer 15 included in controller 13. Obtainer 12 is, for example, a communication interface for wired or wireless communication.

Controller 13 includes outputter 11, analyzer 15, and estimator 16. Controller 13 is implemented specifically by a processor, a microcomputer, or a dedicated circuit.

Storage 14 stores information indicating a state of the oral organs suitable for user 2 to utter a predetermined voice. Storage 14 may also store, for example, the voice data of the voice uttered by user 2 obtained by obtainer 12, data such as the voice feature amounts of user 2's pronunciation analyzed by analyzer 15, the personal information about user 2, and programs executed by outputter 11, obtainer 12, controller 13, analyzer 15, and estimator 16. Storage 14 is implemented by, for example, read-only memory (ROM), random-access memory (RAM), semiconductor memory, or hard disk drive (HDD).

Analyzer 15 analyzes the uttered voice of user 2 obtained by obtainer 12. Analyzer 15 may analyze, from the uttered voice of user 2, the voice feature amounts such as the first formant frequency, the second formant frequency, the sound pressure difference, and the speaking speed as described with reference to FIG. 1, for example. Analyzer 15 is implemented specifically by a processor, a microcomputer, or a dedicated circuit.

Estimator 16 estimates a state of the oral organs of user 2 from the result of the analysis of the uttered voice by analyzer 15. Estimator 16 estimates, from the uttered voice of user 2, a state of the oral cavity of user 2 based on, for example, the parts inside the oral cavity described with reference to FIG. 2. Specifically, estimator 16 may estimate, for example, the positions of the blade of the tongue, front of the tongue, and back of the tongue in the oral cavity or the positional relationship between the upper lip and the lower lip. Estimator 16 is implemented specifically by a processor, a microcomputer, or a dedicated circuit.

[Processing Procedure of Oral Function Visualization System]

Next, the processing performed by oral function visualization system 10 will be described.

Figure 4:
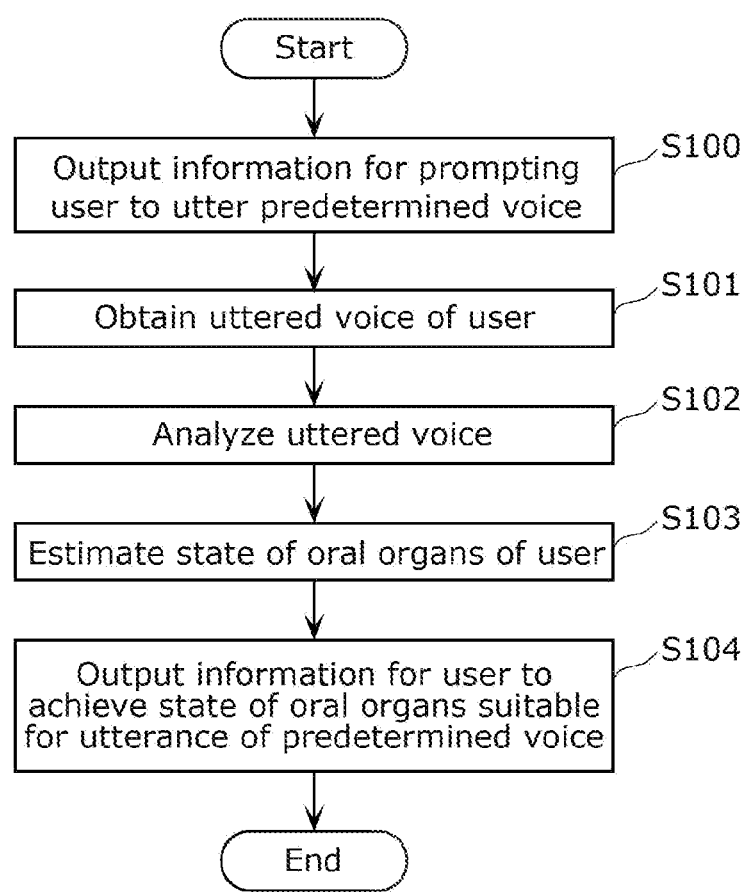
FIG. 4 is a flowchart of operations of the oral function visualization system according to the embodiment of the present disclosure.

FIG. 4 is a flowchart of operations of the oral function visualization system according to the embodiment of the present disclosure.

First, outputter 11 outputs, to the screen, information for prompting user 2 to utter a predetermined voice (step S100). For example, outputter 11 may output an image showing an example sentence or a word for user 2 to pronounce, or may output a voice indicating an example sentence or a word for user 2 to pronounce. For example, outputter 11 may output, to the screen, a character string indicating an example sentence "e wo ka ku ko to ni ki me to (I decided to draw a picture)", a character string indicating syllables such as "kala" and "sala", or a character string indicating a word such as "ippai", "ikkai", or "ittai".

Note that storage 14 may store in advance information indicating a state of the oral organs. For example, storage 14 stores oral cavity state data items which are images each showing a state of the oral organs that is associated with a predetermined voice feature amount. Image data showing a state of the oral organs that is associated with a predetermined voice feature amount will be described later.

Next, obtainer 12 obtains an uttered voice of user 2 (step S101). Obtainer 12 obtains an uttered voice of user 2 through a microphone, for example.

Then, analyzer 15 analyzes the uttered voice of user 2 obtained by obtainer 12 (step S102). Analyzer 15 analyzes the uttered voice of user 2 and extracts voice feature amounts. For example, analyzer 15 analyzes the uttered voice of user 2 to extract the first formant frequency, the second formant frequency, the sound pressure difference, and the like as voice feature amounts.

Next, estimator 16 estimates a state of oral organs of user 2 from the voice feature amounts of the uttered voice of user 2 analyzed by analyzer 15 (step S103). Estimator 16 estimates, for example, the open or closed state of the mouth of user 2 or the positions of the blade of the tongue, front of the tongue, back of the tongue, and root of the tongue of user 2.

Outputter 11 then outputs, to a screen or loudspeaker, etc., information for user 2 to achieve a state of the oral organs suitable for utterance of a predetermined voice (Step S104). Here, a predetermined voice is a voice indicating a word or the like that outputter 11 presented in step S100 for user 2 to pronounce. Outputter 11 may output, as the information for user 2 to achieve a state of the oral organs suitable for utterance of a predetermined voice, a diagram illustrating the state of the oral organs of user 2 estimated by estimator 16 and a diagram illustrating a state of the oral organs suitable for utterance of a predetermined voice. Further, outputter 11 may output, as the information for user 2 to achieve a state of the oral organs suitable for utterance of a predetermined voice, a word indicating the state of the oral organs of user 2 estimated by estimator 16 and a word indicating a state of the oral organs suitable for utterance of a predetermined voice, in the form of, for example, a voice or a character string. At that time, outputter 11 may output a result of comparison between the state of the oral organs of user 2 estimated by estimator 16 and the state of the oral organs suitable for utterance of a predetermined voice. Also, as the information for user 2 to achieve a state of the oral organs suitable for utterance of a predetermined voice, outputter 11 may output advice for achieving a state of the oral organs suitable for utterance of a predetermined voice, in the form of, for example, a voice, a character string, or a diagram.

[Relationship between Formant Vowels and Oral Cavity]

Figure 5:
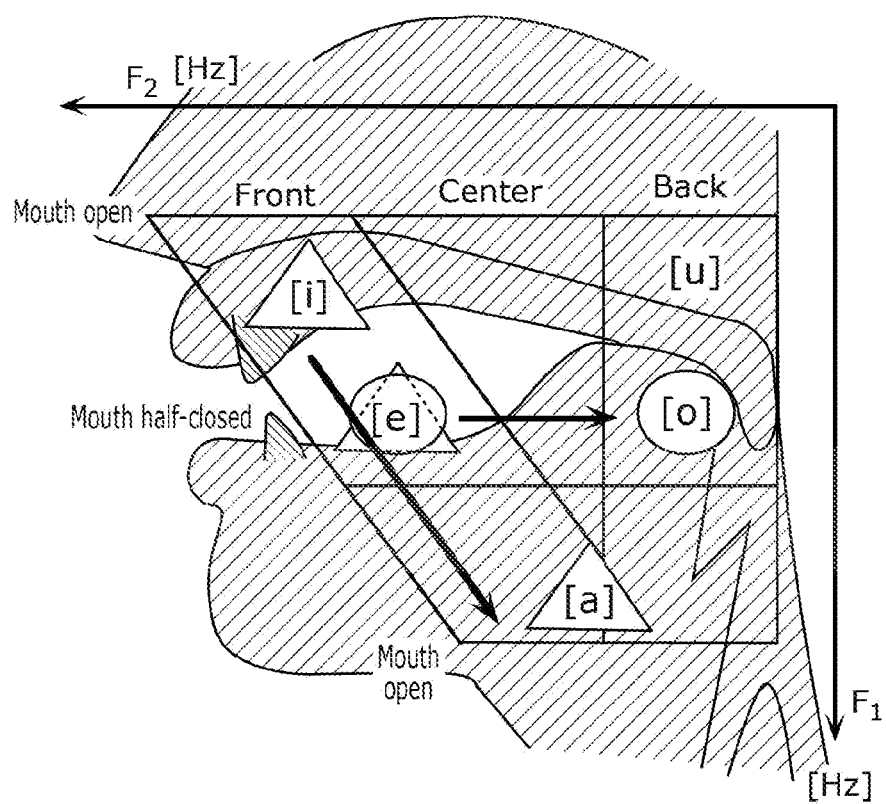
FIG. 5 is a diagram illustrating the relationship between formant vowels and the state of the inside of the oral cavity.

FIG. 5 is a diagram illustrating the relationship between formant vowels and the state of the inside of the oral cavity. As illustrated in FIG. 5, the first formant frequency (denoted by $F_1$) is relevant to the open or closed state of the mouth, and the second formant frequency (denoted by $F_2$) is relevant to the position of the tongue in the oral cavity. Specifically, when the mouth is closed and the tongue is in the front position, the pronunciation is "i". When the mouth is half-closed and the tongue is in the front position, the pronunciation is "e". Next, when the mouth is open and the tongue is in the middle position, the pronunciation is "a". When the mouth is closed and the tongue is in the back position, the pronunciation is "u". When the mouth is half-closed and the tongue is in the back position, the pronunciation is "o".

When the tongue is in the front position, the pronunciations of "i", "e", and "a" have high first formant frequencies in the stated order. When the tongue is in the back position, the pronunciation of "o" has a first formant frequency higher than that of the pronunciation of "u".

When the mouth is closed, the pronunciation of "i" has a second formant frequency higher than that of the pronunciation of "u". When the mouth is half-closed, the pronunciation of "e" has a second formant frequency higher than that of the pronunciation of "o".

[Example of Pronunciation Analysis and Visualization]

Figure 6:
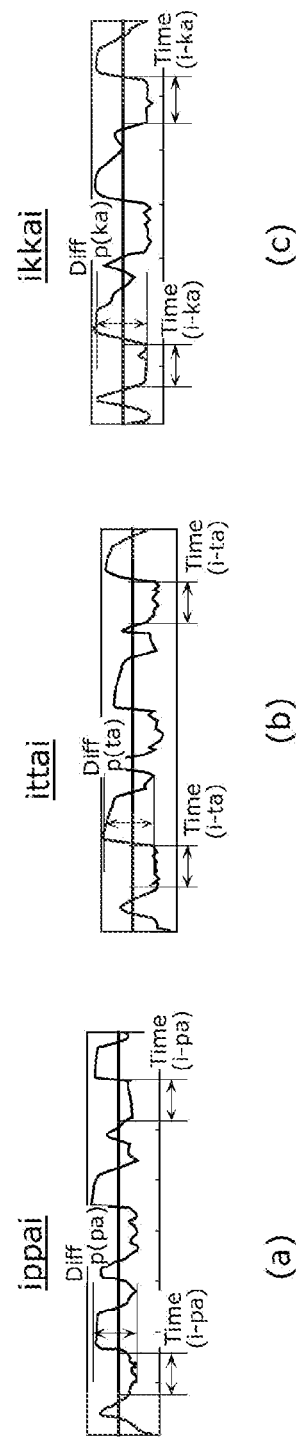
FIG. 6 is a diagram illustrating an example of words used for training on oral functions and an example of waveforms of pronunciations of the words.

FIG. 6 is a diagram illustrating an example of words used for training on oral functions and an example of waveforms of pronunciations of the words. As illustrated in FIG. 6, oral function visualization system 10 causes user 2 to pronounce words "ippai", "ittai", and "ikkai", for example. As illustrated in portions (a), (b), and (c) of FIG. 6, the areas denoted by "Diff" in the graphs indicate that the lips are closed or the tongue is obstructed. Also, as illustrated in portions (a), (b), and (c) of FIG. 6, the areas indicated by "Time" in the graphs indicate the closure period of the lips or the obstruction period of the tongue. In each graph, when the waveform is above the reference line, the intensity of the voice is determined to be a certain level or higher.

Figure 7:
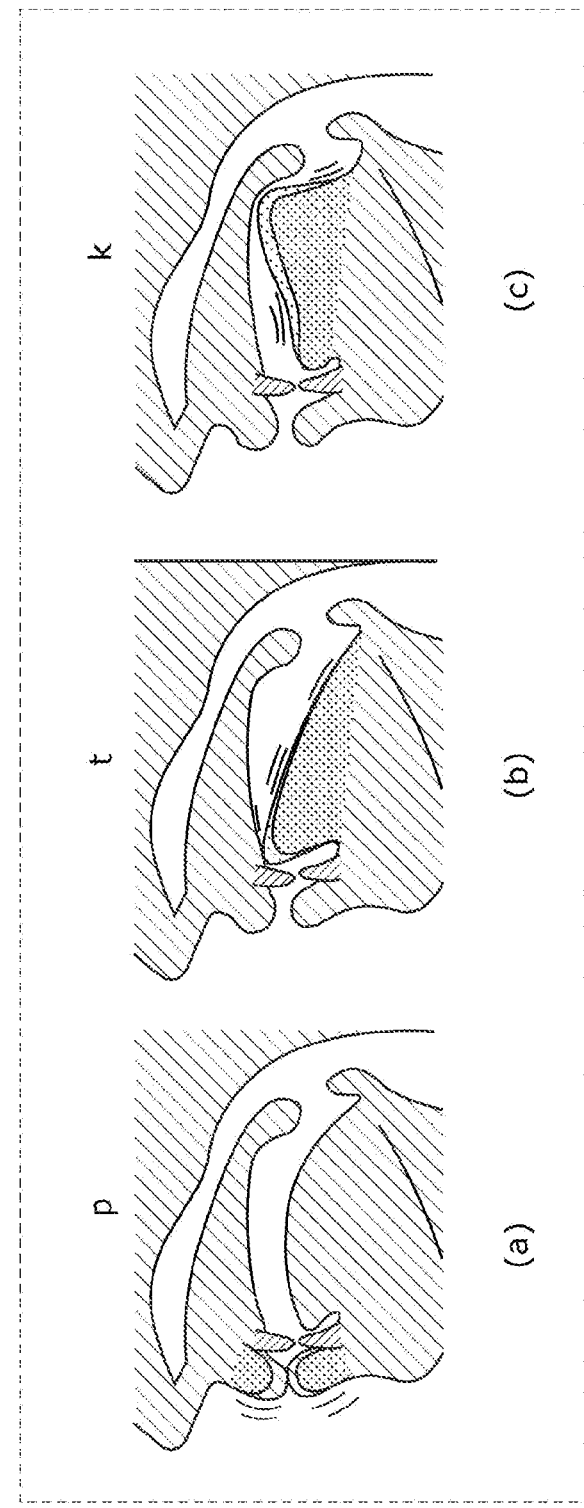
FIG. 7 is a diagram illustrating an example of the states of the inside of the oral cavity when particular consonants are pronounced.

FIG. 7 is a diagram illustrating an example of the states of the inside of the oral cavity when particular consonants are pronounced. First, the case where oral function visualization system 10 causes user 2 to pronounce the word "ippai" will be described. The word "ippai" contains the consonant "p". Thus, as illustrated in portion (a) of FIG. 7, oral function visualization system 10 analyzes whether user 2 is being able to pronounce the word as if user 2 were bursting air after closing the lips completely. When oral function visualization system 10 causes user 2 to pronounce the word "ippai", oral function visualization system 10 may visualize the state of the oral organs of user 2 by emphasizing the movement of the lips in particular.

Next, the case where oral function visualization system 10 causes user 2 to pronounce the word "ittai" will be described. The word "ittai" contains the consonant "t". Thus, as illustrated in portion (b) of FIG. 7, oral function visualization system 10 analyzes whether user 2 is being able to pronounce the word by having the tongue completely touch the gums of the upper part of the oral cavity and then releasing the tongue. When oral function visualization system 10 causes user 2 to pronounce the word "ittai", oral function visualization system 10 may visualize the state of the oral organs of user 2 by emphasizing the movement of the tip of the tongue in particular.

Next, the case where oral function visualization system 10 causes user 2 to pronounce the word "ikkai" will be described. The word "ikkai" contains the consonant "k". Thus, as illustrated in portion (c) of FIG. 7, oral function visualization system 10 analyzes whether user 2 is being able to pronounce the word by having the back of the tongue completely touch the hard palate or the soft palate at the upper part of the oral cavity to close the airway and then opening the airway. When oral function visualization system 10 causes user 2 to pronounce the word "ikkai", oral function visualization system 10 may visualize the state of the oral organs of user 2 by emphasizing the movement of the back of the tongue in particular.

Figure 8:
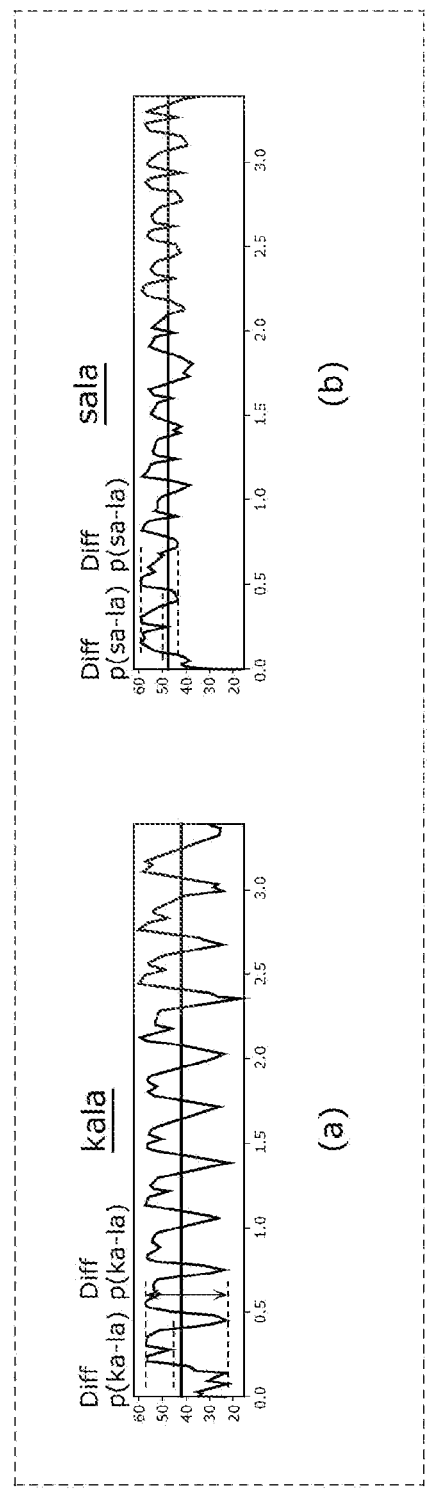
FIG. 8 is a diagram illustrating an example of waveforms of pronunciations of words used for training on oral functions.

FIG. 8 is a diagram illustrating an example of waveforms of pronunciations of words used for training on oral functions. The following describes the case where oral function visualization system 10 causes user 2 to pronounce the words "kala" and "sala". As illustrated in FIG. 8, a waveform in the form of two-humped mountains is observed when the word "kala" or "sala" is pronounced. When the humps of the observed waveform are smooth, it is interpreted that "ka" or "sa" is not pronounced well. If a waveform higher than the reference line is observed, it is interpreted that the voice volume is a certain level or higher.

Figure 9:
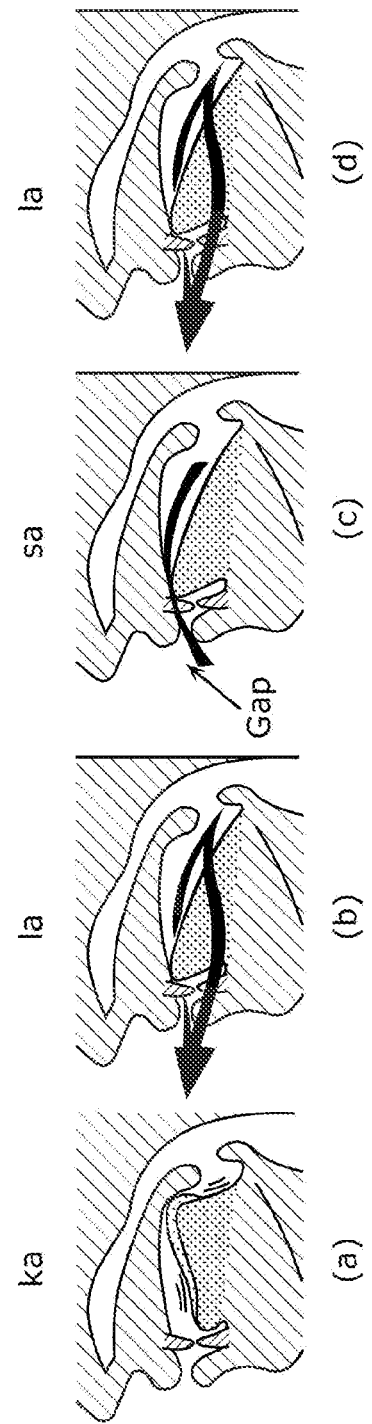
FIG. 9 is a diagram illustrating an example of the states of the inside of the oral cavity when particular consonants are pronounced.

For example, when user 2 pronounces the word "kala", the states of the oral organs as illustrated in portions (a) and (b) of FIG. 9 are shown. Since the pronunciation of "ka" needs the back of the tongue in contact with the hard palate or the soft palate at the upper part of the oral cavity, a diagram in which the back of the tongue is in contact with the hard palate or the soft palate at the upper part of the oral cavity is shown if user 2 is being able to pronounce "ka" perfectly. On the other hand, if user 2 is not being able to pronounce "ka" perfectly, a diagram is shown in which the back of the tongue is not in contact with the hard palate or the soft palate at the upper part of the oral cavity and there is a gap between the tongue and the hard palate or the soft palate.

For example, when user 2 pronounces the word "sala", the states of the oral organs as illustrated in portions (c) and (d) of FIG. 9 are shown. Since the pronunciation of "sa" needs the tip of the tongue in contact with the gum at the upper part of the oral cavity, a diagram in which the tip of the tongue is in contact with the gum at the upper part of the oral cavity is shown if user 2 is being able to pronounce "sa" properly. On the other hand, if user 2 is not being able to pronounce "sa" perfectly, a diagram is shown in which the tip of the tongue is not in contact with the gum at the upper part of the oral cavity and there is a gap between the tongue and the gum. Also, the pronunciation of "sa" needs the lips to be open, and thus a diagram in which there is a gap between the upper and lower lips is shown.

[Example of Output of Oral Function Visualization System]

Figure 10:
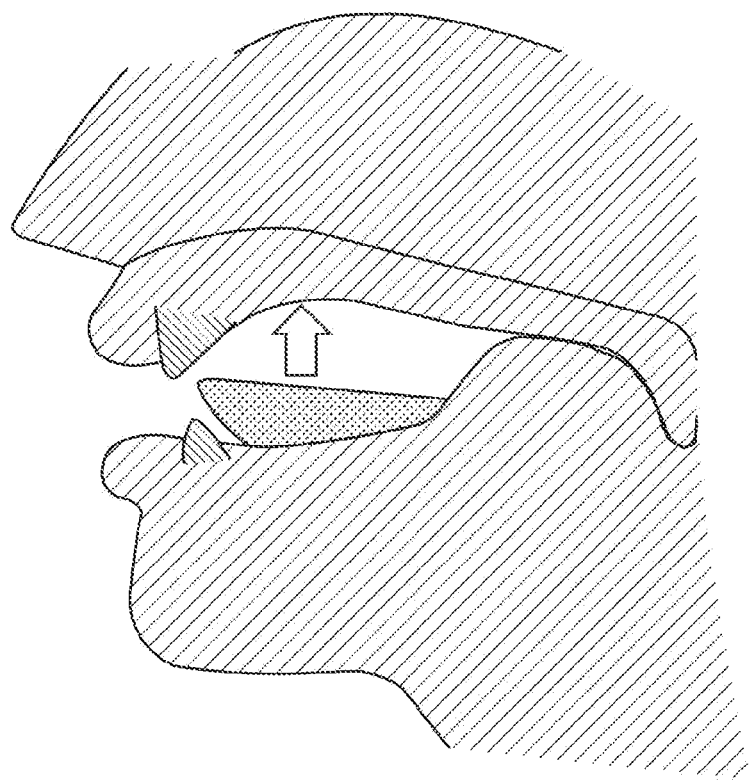
FIG. 10 is a diagram illustrating an example of output of the oral function visualization system according to the embodiment of the present disclosure.

FIG. 10 is a diagram illustrating an example of output of the oral function visualization system according to the embodiment of the present disclosure. The state of the oral organs of user 2 estimated from the voice uttered by user 2 and a state of the oral organs ideal for pronouncing the word that oral function visualization system 10 has caused user 2 to pronounce are illustrated. These two states may be illustrated in one diagram or two separate diagrams. The diagrams output by oral function visualization system 10 may include graphics such as an arrow indicating a direction or the like for improving the positions of the oral organs of user 2. In addition, oral function visualization system 10 may display, for example, a sentence indicating a direction or the like for improving the positions of the oral organs of user 2, or may display, for example, wording that prompts user 2 to further practice the pronunciation, on the screen.

For example, after causing user 2 to pronounce a specific word, oral function visualization system 10 estimates a state of the oral organs of user 2 corresponding to a syllable uttered by user 2 and displays the estimated state using a diagram or words. Oral function visualization system 10 estimates the open or closed state of the mouth of user 2 or the positions of the blade of the tongue, front of the tongue, back of the tongue, and root of the tongue of user 2, and displays the estimated state or positions on the screen using a diagram or words. The estimation may be performed for each syllable uttered by user 2. Oral function visualization system 10 may also display a state of the oral organs ideal for pronouncing the word uttered by user 2, on the screen using a diagram or words. Specifically, oral function visualization system 10 displays, on the screen, a diagram illustrating a state in which the blade of the tongue is oriented toward the gums but is not in contact with the gums, as the state of the oral organs of user 2 corresponding to the syllable uttered by user 2. Oral function visualization system 10 then displays a diagram illustrating a state in which the blade of the tongue is closer to the gums, as the state of the oral organs ideal for pronouncing the word uttered by user 2. An upward arrow prompting the user to move the entire tongue upward may be illustrated at the same time. In addition, a sentence "Raise your tongue a little more." indicating a direction or the like for improving the positions of the oral organs of user 2 may be displayed on the screen. Also, a sentence "Let's practice one more time." may be displayed on the screen as a sentence or the like that prompts user 2 to further practice the pronunciation. Note that such words or the like displayed on the screen may be read aloud.

As described above, oral function visualization system 10 outputs a diagram or words that enable user 2 to achieve the state of the oral organs ideal for pronunciation.

[Example of Image Data Used by Oral Function Visualization System]

Next, the following describes data used for oral function visualization system 10 to estimate and visualize a state of the oral organs of user 2. FIG. 11 is a diagram illustrating an example of data that associates voice feature amounts and image data items used by the oral function visualization system according to the embodiment of the present disclosure.

Oral function visualization system 10 stores, in storage 14, oral cavity state data items which are images each showing a state of the oral organs that is associated with a predetermined voice feature amount. For example, image A is stored in storage 14 as a data item corresponding to the voice "a" having a first formant frequency of 768 Hz, a second formant frequency of 1306 Hz, and a third formant frequency of 2552 Hz. Here, stored in storage 14 are image data items which correspond to, among sounds classified into "a", sounds resulting from various combinations of the first formant frequency, the second formant frequency, and the third formant frequency. The same is true for other types of vowels and consonants. Although the first formant frequency, the second formant frequency, and the third formant frequency are employed here as voice feature amounts, other types of voice feature amounts may be used.

Oral function visualization system 10 then outputs, from outputter 11, oral cavity state data items each corresponding to a voice feature amount obtained as a result of analysis of the uttered voice by analyzer 15. Oral function visualization system 10 selects and outputs an oral cavity state data item (e.g., an image data item) corresponding to voice feature amounts closest to the voice feature amounts of the uttered voice. Oral function visualization system 10 may continuously display plural oral cavity state data items to output them as video.

[Application in Evaluation of Eating and Swallowing]

Oral function visualization system 10 can be applied to, for example, evaluation of eating and swallowing and improvement of the eating and swallowing functions.

First, the eating and swallowing process will be described. The eating and swallowing functions are functions of the human body necessary to accomplish a series of processes from the recognition of food to the intake of the food into the mouth and eventually the stomach. The eating and swallowing functions have five phases: the pre-oral phase, the oral preparatory phase, the oral transit phase, the pharyngeal phase, and the esophageal phase.

In the pre-oral phase (also called the cognitive phase) of eating and swallowing, the shape, hardness, temperature, etc., of food are determined. The eating and swallowing function in the pre-oral phase is, for example, the visual recognition function of the eyes. In the pre-oral phase, the nature and state of the food are recognized, and preparations necessary for eating, such as the eating style, saliva secretion, and posture, are made.

In the oral preparatory phase (also called the mastication phase) of eating and swallowing, food taken into the oral cavity is chewed and ground (i.e., masticated) by teeth, and then the masticated food is mixed with saliva by the tongue to form a bolus. The eating and swallowing functions in the oral preparatory phase include, for example, the motor function of facial muscles (e.g., lip muscles and cheek muscles) to take food into the oral cavity without spilling it, the cognitive function of the tongue to recognize the taste and hardness of food, the motor function of the tongue to press food against the teeth and to mix small pieces of food with saliva to form a bolus, the occlusion of the teeth to chew and grind food, the motor function of the cheeks to prevent food from getting between the teeth and cheeks, the motor function (mastication function) of the masticatory muscles, that is, a general term for the muscles for mastication (e.g., the masseter muscle and temporal muscle), and the saliva secretion function to secrete saliva for mixing with small pieces of food. The mastication function is influenced by, for example, the occlusal state of the teeth, the motor function of the masticatory muscles, and the function of the tongue. With these eating and swallowing functions in the oral preparatory phase, the bolus is given properties (size, lump, viscosity) that enable easy swallowing, so that the bolus can smoothly move from the oral cavity to the stomach through the pharynx.

In the oral transit phase of eating and swallowing, the tongue (the tip of the tongue) is lifted and moves the bolus from the inside of the oral cavity to the pharynx. The eating and swallowing functions in the oral transit phase include, for example, the motor function of the tongue to move the bolus to the pharynx and the ascending function of the soft palate which closes the space between the pharynx and the nasal cavity.

In the pharyngeal phase of eating and swallowing, swallowing reflex occurs when the bolus reaches the pharynx, and the bolus is sent to the esophagus within a short period of time (about one second). Specifically, the soft palate rises to close the space between the nasal cavity and pharynx, the base of the tongue (specifically, the hyoid bone supporting the base of the tongue) and the larynx rise to allow the bolus to pass through the pharynx, at which time the epiglottis flips downward to close the entrance of the trachea and the bolus is sent to the esophagus in a manner that aspiration does not occur. The eating and swallowing functions in the pharyngeal phase include, for example, the motor function of the pharynx to close the space between the nasal cavity and the pharynx (specifically, the motor function to raise the soft palate), the motor function of the tongue (specifically, the base of the tongue) to send the bolus to the pharynx, and the motor function of the larynx to send the bolus from the pharynx to the esophagus and to close the glottis to block the trachea and hang the epiglottis down over it to cover the entrance of the trachea when the bolus flows into the pharynx.

In the esophageal phase of eating and swallowing, peristaltic movement of the esophageal wall is induced and the bolus is sent from the esophagus to the stomach. The eating and swallowing function in the esophageal phase is, for example, the peristaltic function of the esophagus to move the bolus to the stomach.

For example, as a person ages, he/she transits from a healthy state to a state requiring nursing care after going through the pre-frail stage and the frail stage. A decline in the eating and swallowing functions (also called oral frailty) is said to start appearing during the pre-frail stage. A decline in the eating and swallowing functions could hasten the progression to the state requiring nursing care which follows the frail stage. Therefore, by noticing how the eating and swallowing functions are declining in the pre-frail stage and taking preventive and remedial measures in advance, it is possible to reduce the risk of falling into the state requiring nursing care which follows the frail stage and to maintain a healthy and independent life for a longer period of time.

Next, the following describes an example in which oral function visualization system 10 displays on a screen an image of an estimated state of the oral organs of user 2 in accordance with the eating and swallowing process. FIG. 12 is a table showing the contents of video display corresponding to the eating and swallowing process according to the embodiment of the present disclosure.

Oral function visualization system 10 focuses on "i", "e", and "a" as sounds corresponding to the opening and closing of the mouth which is a process in the mastication phase. To evaluate the process of the opening and closing of the mouth, oral function visualization system 10 causes user 2 to pronounce a word containing the sounds "i", "e", and "a", and analyzes user 2's pronunciation. Oral function visualization system 10 then displays on the screen a state of the oral organs of user 2 which is estimated from user 2's pronunciation. At this time, oral function visualization system 10 may also display a state of the oral organs ideal for pronouncing the word containing the sounds "i", "e", and "a".

Also, for example, oral function visualization system 10 focuses on "ka la" as a sound corresponding to mastication which is a process in the mastication phase. To evaluate the process of the opening and closing of the mouth, oral function visualization system 10 causes user 2 to pronounce a word containing the sound "ka la", and analyzes user 2's pronunciation. Oral function visualization system 10 then displays on the screen a state of the oral organs of user 2 which is estimated from user 2's pronunciation. At this time, oral function visualization system 10 may also display a state of the oral organs ideal for pronouncing the word containing the sound "ka la".

Also, for example, oral function visualization system 10 focuses on "p" as a sound corresponding to lip closure which is a process in the mastication phase. To evaluate the process of the opening and closing of the mouth, oral function visualization system 10 causes user 2 to pronounce a word containing the sound "p", and analyzes user 2's pronunciation. Oral function visualization system 10 then displays on the screen a state of the oral organs of user 2 which is estimated from user 2's pronunciation. At this time, oral function visualization system 10 may also display a state of the oral organs ideal for pronouncing the word containing the sound "p".

Also, for example, oral function visualization system 10 focuses on "t" and "e" as sounds corresponding to forward tongue movement which is a process in the oral transit phase. To evaluate the process of forward tongue movement, oral function visualization system 10 causes user 2 to pronounce a word containing the sounds "t" and "e", and analyzes user 2's pronunciation. Oral function visualization system 10 then displays on the screen a state of the oral organs of user 2 which is estimated from user 2's pronunciation. At this time, oral function visualization system 10 may also display a state of the oral organs ideal for pronouncing the word containing the sounds "t" and "e".

Also, for example, oral function visualization system 10 focuses on "k" and "o" as sounds corresponding to back tongue movement which is a process in the oral transit phase. To evaluate the process of back tongue movement, oral function visualization system 10 causes user 2 to pronounce a word containing the sounds "k" and "o", and analyzes user 2's pronunciation. Oral function visualization system 10 then displays on the screen a state of the oral organs of user 2 which is estimated from user 2's pronunciation. At this time, oral function visualization system 10 may also display a state of the oral organs ideal for pronouncing the word containing the sounds "k" and "o".

Also, for example, oral function visualization system 10 focuses on "ko" as a sound corresponding to tongue palate closure which is a process in the pharyngeal phase. To evaluate the process of tongue palate closure, oral function visualization system 10 causes user 2 to pronounce a word containing the sound "ko", and analyzes user 2's pronunciation. Oral function visualization system 10 then displays on the screen a state of the oral organs of user 2 which is estimated from user 2's pronunciation. At this time, oral function visualization system 10 may also display a state of the oral organs ideal for pronouncing the word containing the sound "ko".

In this way, oral function visualization system 10 can evaluate the eating and swallowing functions of user 2 by analyzing user 2's pronunciation. Oral function visualization system 10 can also prompt user 2 to do training for improving the eating and swallowing functions, by analyzing user 2's pronunciation and displaying an estimated state of the oral organs of user 2 on the screen. In such a manner, oral function visualization system 10 can be applied to, for example, the evaluation of eating and swallowing and improvement of the eating and swallowing functions.

[Advantageous Effects etc.]

Oral function visualization system 10 includes: outputter 11 that outputs information for prompting user 2 to utter a predetermined voice; obtainer 12 that obtains an uttered voice of user 2 uttered in accordance with the output; analyzer 15 that analyzes the uttered voice obtained by obtainer 12; and estimator 16 that estimates a state of oral organs of user 2 from a result of analysis of the uttered voice by analyzer 15. Outputter 11 outputs, based on the state of the oral organs of user 2 estimated by estimator 16, information for user 2 to achieve a state of the oral organs suitable for utterance of the predetermined voice.

Accordingly, oral function visualization system 10 can visualize the inside of the oral cavity of user 2 that is based on user 2's pronunciation, by displaying a state of the oral organs on the screen, for example. Since user 2 can recognize the state of the oral organs outputted, user 2 can try to utter a voice correctly. As a result, user 2 will be able to utter a voice correctly.

Oral function visualization system 10 includes storage 14 that stores information indicating a state of the oral organs suitable for utterance of the predetermined voice. Storage 14 further stores the an uttered voice of user 2 uttered in the past. Outputter 11 reproduces a state of the oral organs of user 2 estimated by estimator 16 from the uttered voice of user 2 uttered in the past and stored in storage 14, reproduces a state of the oral organs of user 2 estimated by estimator 16 from an uttered voice uttered at present and obtained by obtainer 12, and displays on a screen each of the states of the oral organs reproduced.

Accordingly, by estimating and reproducing states of the oral organs of user 2, oral function visualization system 10 can prompt user 2 to utter the predetermined voice correctly.

Oral function visualization system 10 further includes storage 14 that stores an image showing the state of the oral organs suitable for utterance of the predetermined voice. Estimator 16 generates an image showing the state of the oral organs of user 2 estimated. Outputter 11 displays on the screen the image stored in storage 14 generated by estimator 16.

Accordingly, by displaying on the screen a state of the oral organs ideal for utterance of the predetermined voice and the estimated state of the oral organs of user 2, oral function visualization system 10 can prompt user 2 to utter the predetermined voice correctly.

Outputter 11 shows, as a state of the oral organs, a position of a tongue in an oral cavity and an open or closed state of the oral cavity, using a cross-sectional view of an inside of the oral cavity in a lateral view of a person's face.

Outputter 11 further outputs information that prompts user 2 to do training to achieve the state of the oral organs suitable for utterance of the predetermined voice.

Accordingly, oral function visualization system 10 can prompt user 2 to do training on uttering the predetermined voice.

Storage 14 further stores oral cavity state data items which are images each showing a state of the oral organs that is associated with a predetermined voice feature amount. Outputter 11 outputs the oral cavity state data items each corresponding to a voice feature amount obtained as a result of analysis of the uttered voice by analyzer 15.

Accordingly, using plural images stored in advance, oral function visualization system 10 can reproduce the state of the oral organs of user 2 estimated by estimator 16.

In oral function visualization system 10, each of the images is video.

Accordingly, with use of video, oral function visualization system 10 can prompt user 2 to utter the predetermined voice correctly.

Outputter 11 outputs on paper any or all of at least one of: information for user 2 to achieve the state of the oral organs suitable for utterance of the predetermined voice; information indicating the state of the oral organs suitable for utterance of the predetermined voice; or information that prompts user 2 to do training to achieve the state of the oral organs suitable for utterance of the predetermined voice.

Accordingly, with use of a report provided on paper, oral function visualization system 10 can prompt user 2 to utter the predetermined voice correctly.

An oral function visualization method includes: outputting information for prompting user 2 to utter a predetermined voice; obtaining an uttered voice of user 2 uttered in accordance with the outputting; analyzing the uttered voice obtained in the obtaining; and estimating a state of oral organs of user 2 from a result of analysis of the uttered voice in the analyzing; and outputting, based on the state of the oral organs of user 2 estimated in the estimating, information for user 2 to achieve a state of the oral organs suitable for utterance of the predetermined voice.

Accordingly, the oral function visualization method can yield the same advantageous effects as those yielded by oral function visualization system 10 described above.

A non-transitory computer-readable recording medium has recorded thereon a program that causes a computer to execute an oral function visualization method including: outputting information for prompting user 2 to utter a predetermined voice; obtaining an uttered voice of user 2 uttered in accordance with the outputting; analyzing the uttered voice obtained in the obtaining; estimating a state of oral organs of user 2 from a result of analysis of the uttered voice in the analyzing; and outputting, based on the state of the oral organs of user 2 estimated in the estimating, information for user 2 to achieve a state of the oral organs suitable for utterance of the predetermined voice.

Accordingly, the recording medium can yield the same advantageous effects as those yielded by oral function visualization system 10 described above.

[Other]

Although an embodiment has been described above, the present disclosure is not limited to the above embodiment. For example, the oral function visualization system according to the above embodiment may be implemented by plural devices or may be implemented as a single device. For example, the oral function visualization system may be implemented as a client server system. Also, the oral function visualization system may be implemented as a discrete mobile terminal such as a smartphone or a tablet terminal. In the case of implementing the oral function visualization system using plural devices, the constituent elements of the oral function visualization system may be allocated to the plural devices in any manner.

In the above embodiment, a process performed by a particular processing unit may be performed by another processing unit. The processing order of plural processes may be changed, and plural processes may be performed in parallel.

In addition, in the above embodiment, each constituent element may be implemented through execution of a software program suitable for the constituent element. Each constituent element may also be implemented by a program executing unit such as CPU or a processor reading and executing a software program recorded on a recording medium such as a hard disk or semiconductor memory.

Furthermore, each constituent element may be implemented in the form of a hardware product. For example, each constituent element may be a circuit (or an integrated circuit). These circuits may be configured as a single circuit or may be individual circuits. Moreover, these circuits may be general-purpose circuits, or may be dedicated circuits.

Furthermore, general or specific aspects of the present disclosure may be implemented by a system, a device, a method, an integrated circuit, a computer program, or a computer-readable recording medium such CD-ROM. General or specific aspects of the present disclosure may also be implemented by any combination of systems, devices, methods, integrated circuits, computer programs, and recording media.

For example, the present disclosure may be implemented as a program that causes a computer to execute the oral function visualization method according to the above embodiment. The present disclosure may be implemented as a non-transitory computer-readable recording medium having the program recorded thereon. Note that the program includes an application program for causing a general-purpose mobile terminal to operate as the oral function visualization system according to the above embodiment.

The present disclosure also encompasses other forms achieved by making various modifications to the embodiment that are conceivable to those skilled in the art or forms resulting from any combination of the constituent elements and functions in the embodiment without departing from the essence of the present disclosure.

The invention claimed is:

1. An oral function visualization system comprising:
   an outputter that outputs information for prompting a user to utter a predetermined voice;
   an obtainer that obtains a first uttered voice of the user uttered in accordance with outputting the information by the outputter;
   an analyzer that analyzes a sound pressure difference and a speaking speed of the first uttered voice obtained by the obtainer; and
   an estimator that estimates a first state of oral organs of the user from a result of analysis of the first uttered voice by the analyzer,
   wherein the outputter further outputs, based on the first state of the oral organs of the user estimated by the estimator, information for the user to achieve an ideal state of the oral organs suitable for utterance of the predetermined voice.

2. The oral function visualization system according to claim 1, comprising:
storage that stores (i) information indicating the ideal state of the oral organs suitable for utterance of the predetermined voice and (ii) a second uttered voice of the user uttered in past,
wherein the outputter reproduces the first state, at present, of the oral organs of the user estimated by the estimator from the second uttered voice of the user uttered in past and stored in the storage, reproduces a second state, in past, of the oral organs of the user estimated by the estimator from the first uttered voice uttered at present and obtained by the obtainer, and displays on a screen each of the states of the oral organs reproduced.

3. The oral function visualization system according to claim 2,
wherein the outputter shows the first state of the oral organs at present and the second state of the oral organs in past by a position of a tongue in an oral cavity and an open or closed state of the oral cavity, using a cross-sectional view of an inside of the oral cavity in a lateral view of a person's face.

4. The oral function visualization system according to claim 2,
wherein the storage further stores oral cavity state data items which are images each showing a state of the oral organs that is associated with a predetermined voice feature amount, and
the outputter outputs the oral cavity state data items each corresponding to a voice feature amount obtained as a result of analysis of the first uttered voice by the analyzer.

5. The oral function visualization system according to claim 4,
wherein each of the images is video.

6. The oral function visualization system according to claim 1, further comprising:
storage that stores an image showing the ideal state of the oral organs suitable for utterance of the predetermined voice,
wherein the estimator generates an image showing the first state of the oral organs of the user estimated, and
the outputter displays on a screen the image stored in the storage and the image generated by the estimator.

7. The oral function visualization system according to claim 1,
wherein the outputter further outputs information that prompts the user to do training to achieve the ideal state of the oral organs suitable for utterance of the predetermined voice.

8. The oral function visualization system according to claim 1,
the outputter outputs on paper at least one of: information for the user to achieve the ideal state of the oral organs suitable for utterance of the predetermined voice; information indicating the ideal state of the oral organs suitable for utterance of the predetermined voice; or information that prompts the user to do training to achieve the ideal state of the oral organs suitable for utterance of the predetermined voice.

9. An oral function visualization method comprising:
outputting information for prompting a user to utter a predetermined voice;
obtaining an uttered voice of the user uttered in accordance with outputting the information;
analyzing a sound pressure difference and a speaking speed of the uttered voice obtained in the obtaining;
estimating a first state of oral organs of the user from a result of analysis of the uttered voice in the analyzing; and
outputting, based on the first state of the oral organs of the user estimated in the estimating, information for the user to achieve an ideal state of the oral organs suitable for utterance of the predetermined voice.

10. A non-transitory computer-readable recording medium having recorded thereon a program for causing a computer to execute the oral function visualization method according to claim 9.

* * * * *